United States Patent
Korman et al.

(10) Patent No.: US 11,660,201 B2
(45) Date of Patent: May 30, 2023

(54) SYSTEMS, APPARATUSES, AND METHODS FOR CORRECTING A BONE DEFECT

(71) Applicant: Wright Medical Technology, Inc., Memphis, TN (US)

(72) Inventors: Zachary Korman, Memphis, TN (US); Erin Muller, Lakeland, TN (US); Brian Robert Thoren, Memphis, TN (US); Paul Luttrell, Germantown, TN (US); Bryan D. Den Hartog, St. Paul, MN (US); David B. Kay, Akron, OH (US); Anthony Perera, Pentwyn CARDIFF (GB)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 152 days.

(21) Appl. No.: 16/170,250

(22) Filed: Oct. 25, 2018

(65) Prior Publication Data

US 2020/0129304 A1  Apr. 30, 2020

(51) Int. Cl.
*A61F 2/42* (2006.01)
*A61B 17/92* (2006.01)
(Continued)

(52) U.S. Cl.
CPC ........ *A61F 2/4225* (2013.01); *A61B 17/1682* (2013.01); *A61B 17/1775* (2016.11); *A61B 17/7291* (2013.01); *A61B 17/90* (2021.08); *A61B 17/921* (2013.01); *A61F 2/4606* (2013.01); *A61F 2002/4233* (2013.01); *A61F 2002/4629* (2013.01);
(Continued)

(58) Field of Classification Search
CPC ............... A61B 17/7291; A61B 17/921; A61F 2/4225–2002/4238
See application file for complete search history.

(56) References Cited

U.S. PATENT DOCUMENTS

| | | |
|---|---|---|
| 2,612,159 A | 9/1952 | Collison |
| 6,203,545 B1 | 3/2001 | Stofella |
| (Continued) | | |

FOREIGN PATENT DOCUMENTS

| | | |
|---|---|---|
| CN | 101043854 A | 9/2007 |
| CN | 204072294 U | 1/2015 |
| (Continued) | | |

OTHER PUBLICATIONS

U.S. Appl. No. 62/578,046, filed Oct. 27, 2017.*
(Continued)

*Primary Examiner* — David H Willse
(74) *Attorney, Agent, or Firm* — Duane Morris LLP

(57) ABSTRACT

An implant having a unitary body includes an intramedullary portion and an extramedullary portion. The intramedullary portion is sized and structured to be received within an intramedullary canal of a first bone and defines a longitudinal axis. The extramedullary portion includes a surface defining an axis that is disposed at an angle with respect to the longitudinal axis. An aperture defined along the extramedullary portion is sized and configured to receive a fastener therein for coupling the extramedullary portion of the implant to a second bone.

14 Claims, 14 Drawing Sheets

(51) Int. Cl.
  *A61B 17/90* (2006.01)
  *A61F 2/46* (2006.01)
  *A61B 17/72* (2006.01)
  *A61B 17/17* (2006.01)
  *A61B 17/16* (2006.01)

(52) U.S. Cl.
  CPC .............. *A61F 2002/4681* (2013.01); *A61F 2310/00017* (2013.01); *A61F 2310/00023* (2013.01); *A61F 2310/00029* (2013.01); *A61F 2310/00035* (2013.01); *A61F 2310/00041* (2013.01); *A61F 2310/00047* (2013.01); *A61F 2310/00065* (2013.01); *A61F 2310/00083* (2013.01); *A61F 2310/00359* (2013.01); *A61F 2310/00365* (2013.01); *A61F 2310/00419* (2013.01); *A61F 2310/00928* (2013.01); *A61F 2310/00958* (2013.01)

(56) References Cited

U.S. PATENT DOCUMENTS

| | | |
|---|---|---|
| 6,248,109 B1 | 6/2001 | Stofella |
| 6,689,136 B2 | 2/2004 | Stofella |
| 6,706,046 B2 | 3/2004 | Orbay et al. |
| 6,926,720 B2 | 8/2005 | Castaneda |
| 7,563,263 B2 | 7/2009 | Orbay et al. |
| 7,686,808 B2 | 3/2010 | Orbay et al. |
| 7,727,264 B2 | 6/2010 | Orbay et al. |
| 7,927,341 B2 | 4/2011 | Orbay et al. |
| 7,938,850 B2 | 5/2011 | Orbay et al. |
| 8,083,783 B2 | 12/2011 | Ullman et al. |
| 8,167,918 B2 | 5/2012 | Strnad et al. |
| 8,608,783 B2 | 12/2013 | Graham et al. |
| 8,628,533 B2 | 1/2014 | Graham et al. |
| 8,685,024 B2 | 4/2014 | Roman |
| 8,715,325 B2 | 5/2014 | Weiner et al. |
| 8,753,343 B2 | 6/2014 | Staeubli |
| 8,858,602 B2 | 10/2014 | Weiner et al. |
| 8,888,778 B2 | 11/2014 | Roman |
| 8,926,612 B2 | 1/2015 | Graham |
| 8,998,999 B2 | 4/2015 | Lewis et al. |
| 9,017,329 B2 | 4/2015 | Tyber et al. |
| 9,226,783 B2 | 1/2016 | Brigido |
| 9,452,002 B2 | 9/2016 | Roman et al. |
| 9,486,258 B2 | 11/2016 | Roman et al. |
| 9,554,916 B2 | 1/2017 | Miller |
| 9,597,130 B2 | 3/2017 | Pappalardo et al. |
| 9,615,873 B2 | 4/2017 | Weiner et al. |
| 9,629,671 B2 | 4/2017 | Roman |
| 9,717,543 B2 | 4/2017 | Brown et al. |
| 9,642,656 B2 | 5/2017 | Kotuljac et al. |
| 9,675,391 B2 | 6/2017 | Roman et al. |
| 9,788,871 B2 | 10/2017 | Simon |
| 9,867,642 B2 | 1/2018 | Simon |
| 9,907,562 B2 | 3/2018 | Dacosta et al. |
| 9,943,347 B2 | 4/2018 | Wayne et al. |
| 10,080,597 B2 | 9/2018 | Shemwell et al. |
| 2005/0033302 A1 | 2/2005 | Frank |
| 2006/0015123 A1 | 1/2006 | Fencl et al. |
| 2006/0100624 A1 | 5/2006 | Orbay et al. |
| 2006/0149257 A1 | 7/2006 | Orbay |
| 2006/0161156 A1 | 7/2006 | Orbay |
| 2006/0206044 A1 | 9/2006 | Simon |
| 2007/0083202 A1 | 4/2007 | Running et al. |
| 2007/0191855 A1* | 8/2007 | Orbay ................ A61B 17/7291 606/87 |
| 2007/0233134 A1* | 10/2007 | Bastian ................ A61F 2/4607 606/85 |
| 2009/0036931 A1 | 2/2009 | Pech et al. |
| 2009/0069812 A1 | 3/2009 | Gillard et al. |
| 2009/0118769 A1 | 5/2009 | Sixto, Jr. et al. |
| 2009/0118770 A1 | 5/2009 | Sixto, Jr. et al. |
| 2010/0274293 A1 | 10/2010 | Terrill et al. |
| 2011/0137313 A1 | 9/2011 | Jensen et al. |
| 2012/0016426 A1 | 1/2012 | Robinson |
| 2013/0066383 A1 | 3/2013 | Anderson et al. |
| 2013/0123862 A1 | 5/2013 | Anderson et al. |
| 2014/0018812 A1 | 1/2014 | Graham |
| 2014/0107798 A1 | 4/2014 | Jeng et al. |
| 2014/0180348 A1 | 6/2014 | Thoren et al. |
| 2014/0243837 A1 | 8/2014 | Mebarak |
| 2014/0277178 A1 | 9/2014 | O'Kane et al. |
| 2015/0032168 A1 | 1/2015 | Orsak et al. |
| 2015/0164565 A1 | 6/2015 | Johnson et al. |
| 2016/0051295 A1 | 2/2016 | Nakamura et al. |
| 2016/0074079 A1 | 3/2016 | Leemrijse et al. |
| 2016/0143675 A1 | 5/2016 | Tsai et al. |
| 2016/0157900 A1 | 6/2016 | Simon |
| 2016/0157902 A1 | 6/2016 | Simon |
| 2016/0199110 A1 | 7/2016 | Austin et al. |
| 2016/0354127 A1* | 12/2016 | Lundquist ............ A61B 17/809 |
| 2017/0196602 A1* | 7/2017 | Lundquist ............ A61B 17/809 |
| 2017/0245902 A1* | 8/2017 | Hollis ................ A61B 17/8861 |
| 2018/0028242 A1* | 2/2018 | Parekh ............... A61B 17/8057 |
| 2019/0125418 A1* | 5/2019 | Muller ................ A61B 17/164 |

FOREIGN PATENT DOCUMENTS

| | | | |
|---|---|---|---|
| CN | 204655083 U | 9/2015 | |
| CN | 105997215 A | 10/2016 | |
| EP | 2 228 026 A1 * | 9/2010 | ............ A61B 17/68 |
| EP | 2938279 A1 | 11/2015 | |
| JP | 2015155032 A | 3/2015 | |
| JP | 2015044053 A | 8/2015 | |
| WO | 2011002903 A2 | 1/2011 | |
| WO | 2014105750 A1 | 7/2014 | |

OTHER PUBLICATIONS

Ortholoc 3DI Crosscheck Plating System, Wright Medical Group, http://www.wright.com/footandankleproducts/ortholoc-3di-crosscheckplating-system, Aug. 17, 2017.
Hallux 360, Wright Medical Group, Apr. 2017.
Office Action issued in connection with corresponding Canadian Patent Application No. 3,021,444, dated Jul. 8, 2020, 5 pages.
Office Action issued in connection with corresponding Canadian Patent Application No. 3,021,444, dated Oct. 1, 2019, 6 pages.
Third Examination Report issued in connection with corresponding Australian Patent Application No. 2017325993, dated Nov. 25, 2019, 6 pages.
First Examination Report issued in connection with corresponding Australian Patent Application No. 2018253511, 10 pages, dated Mar. 4, 2019.
Partial Search Report issued in connection with corresponding European Patent Application No. 18202235.0, 10 pages, dated Mar. 7, 2019.
First Office Action issued in connection with corresponding Chinese Patent Application No. 201811248244.6, dated Nov. 30, 2020, 13 pages.
Office Action issued in connection with corresponding Canadian Patent Application No. 3,021,444, dated Mar. 30, 2021, 6 pages.

* cited by examiner

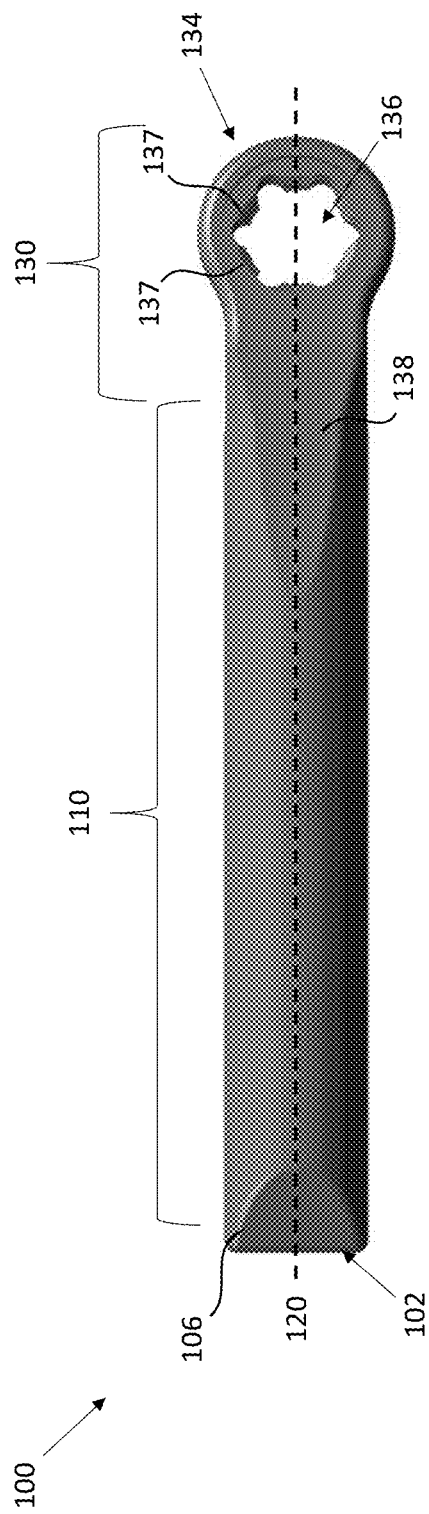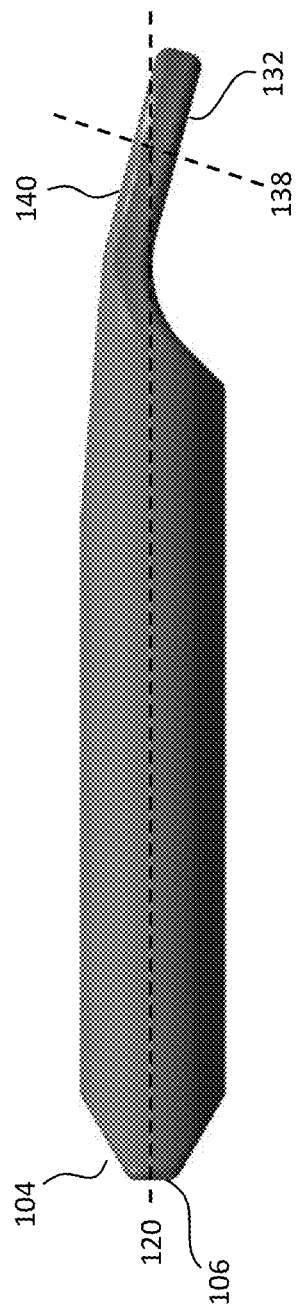
FIG. 1
FIG. 2

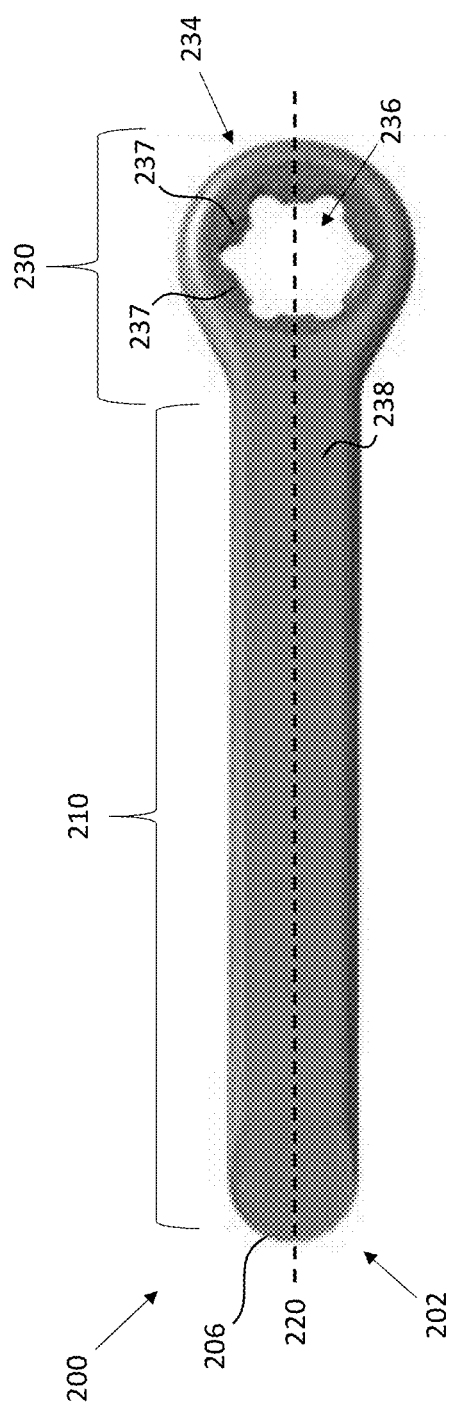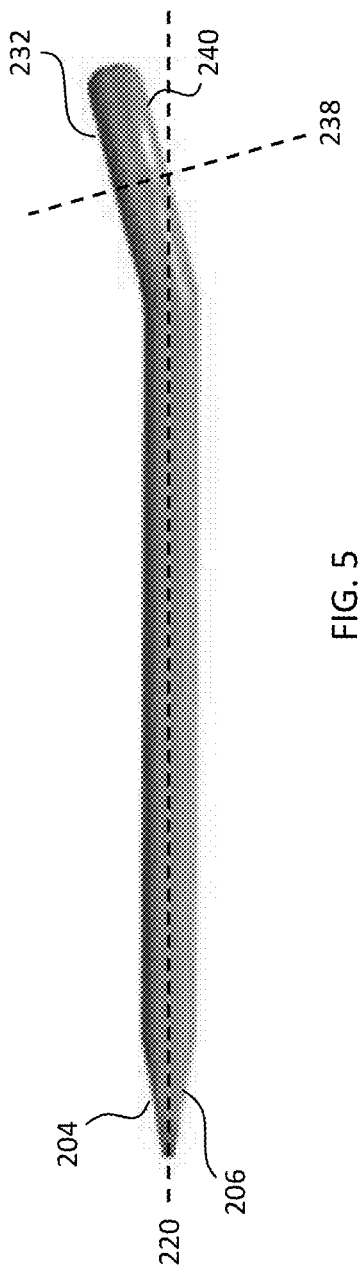
FIG. 4
FIG. 5

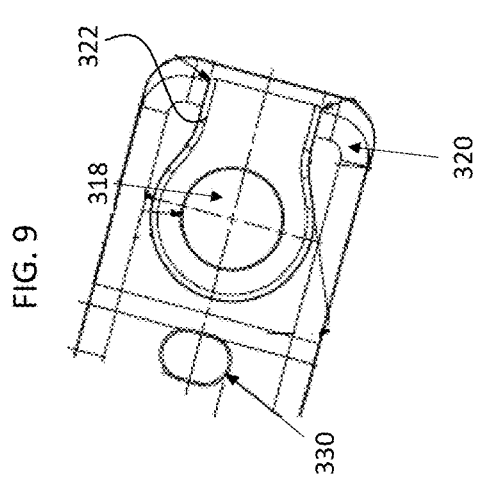
FIG. 9
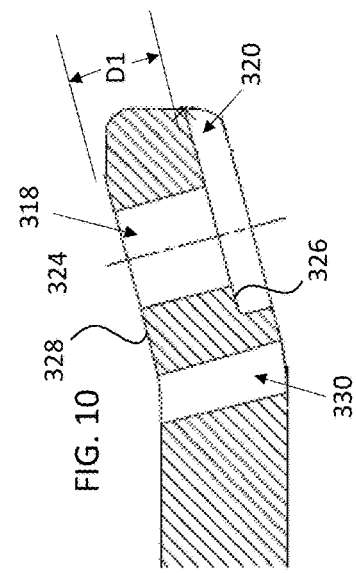
FIG. 10
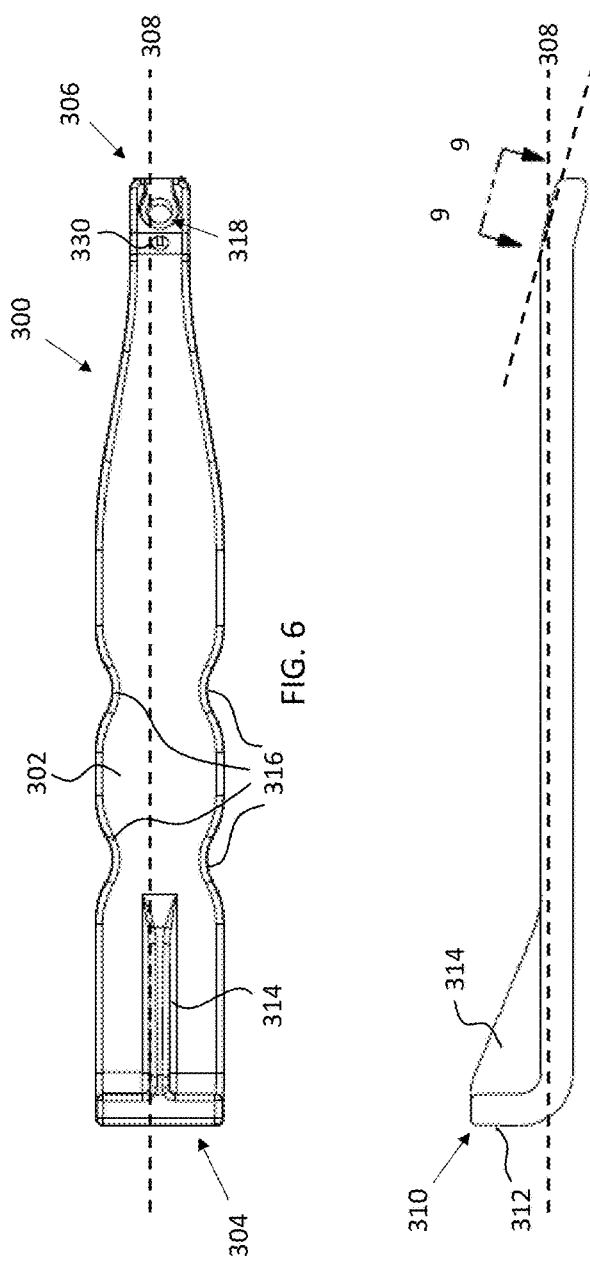
FIG. 6
FIG. 7
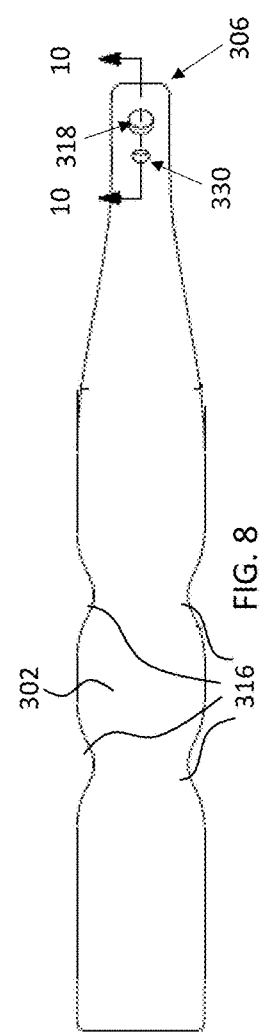
FIG. 8

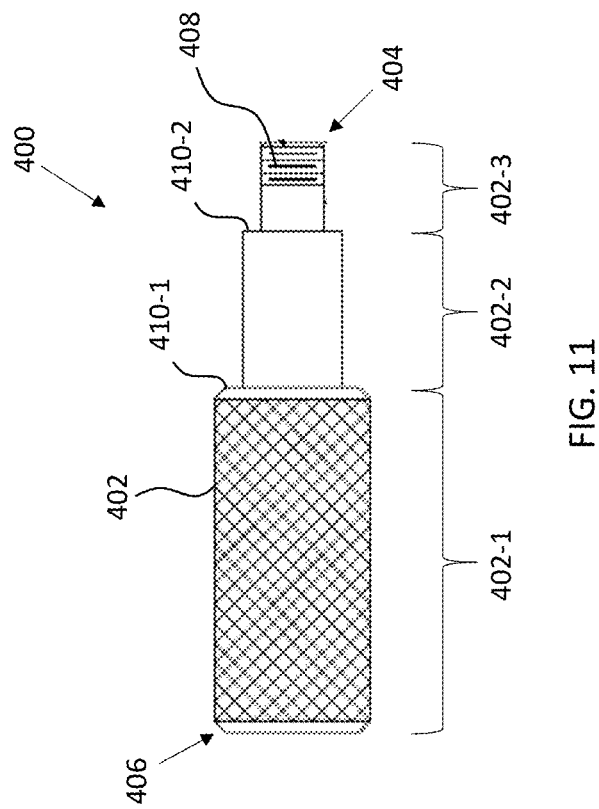
FIG. 11
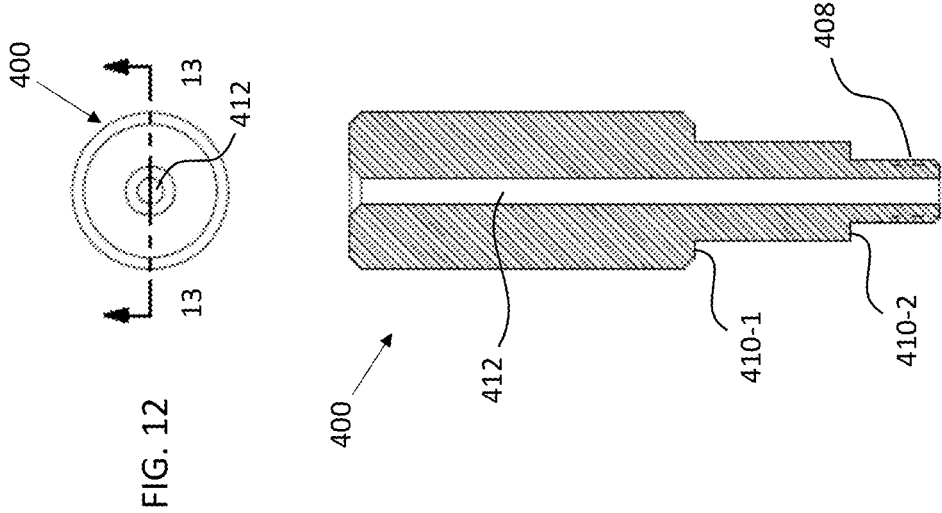
FIG. 12
FIG. 13

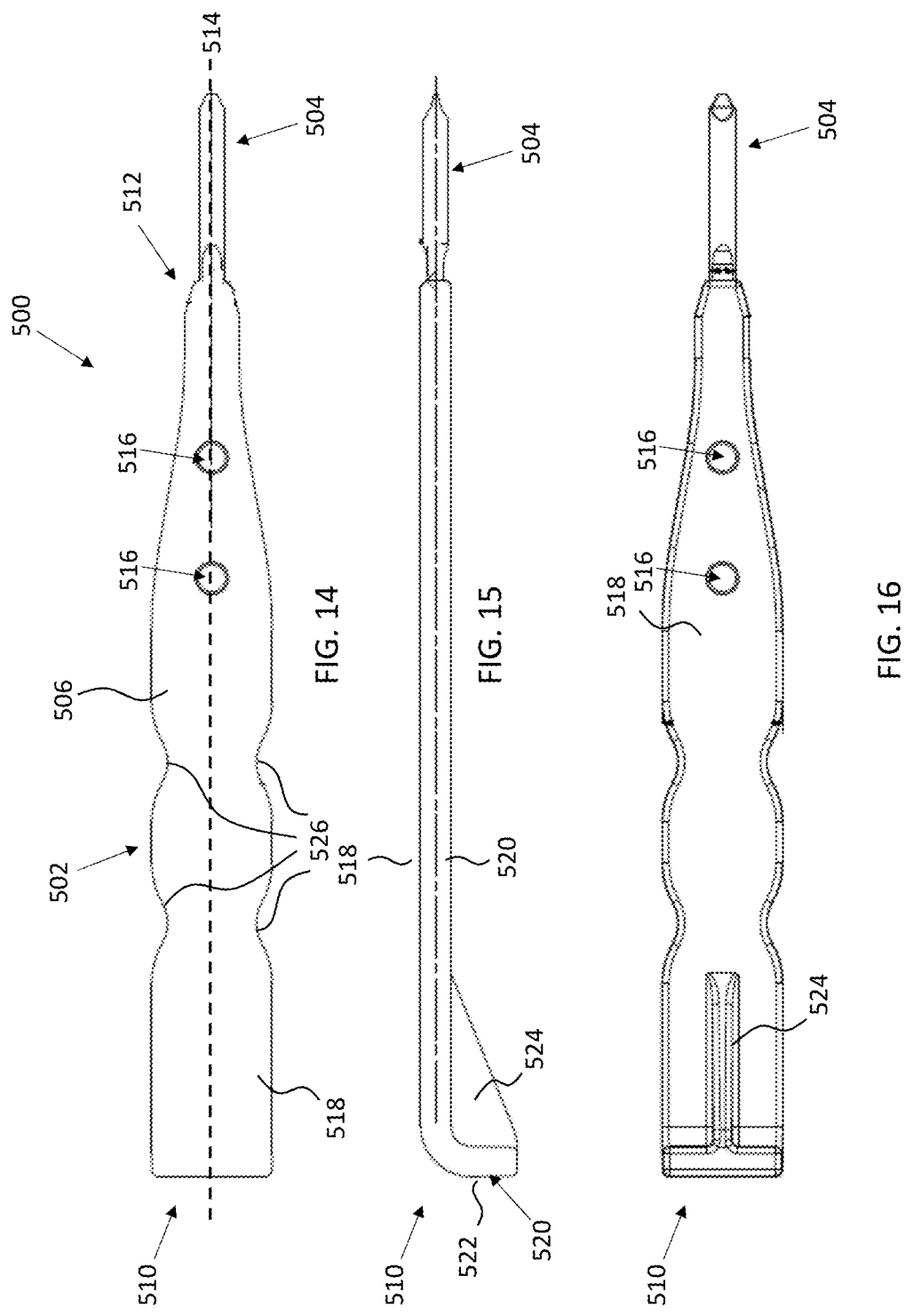

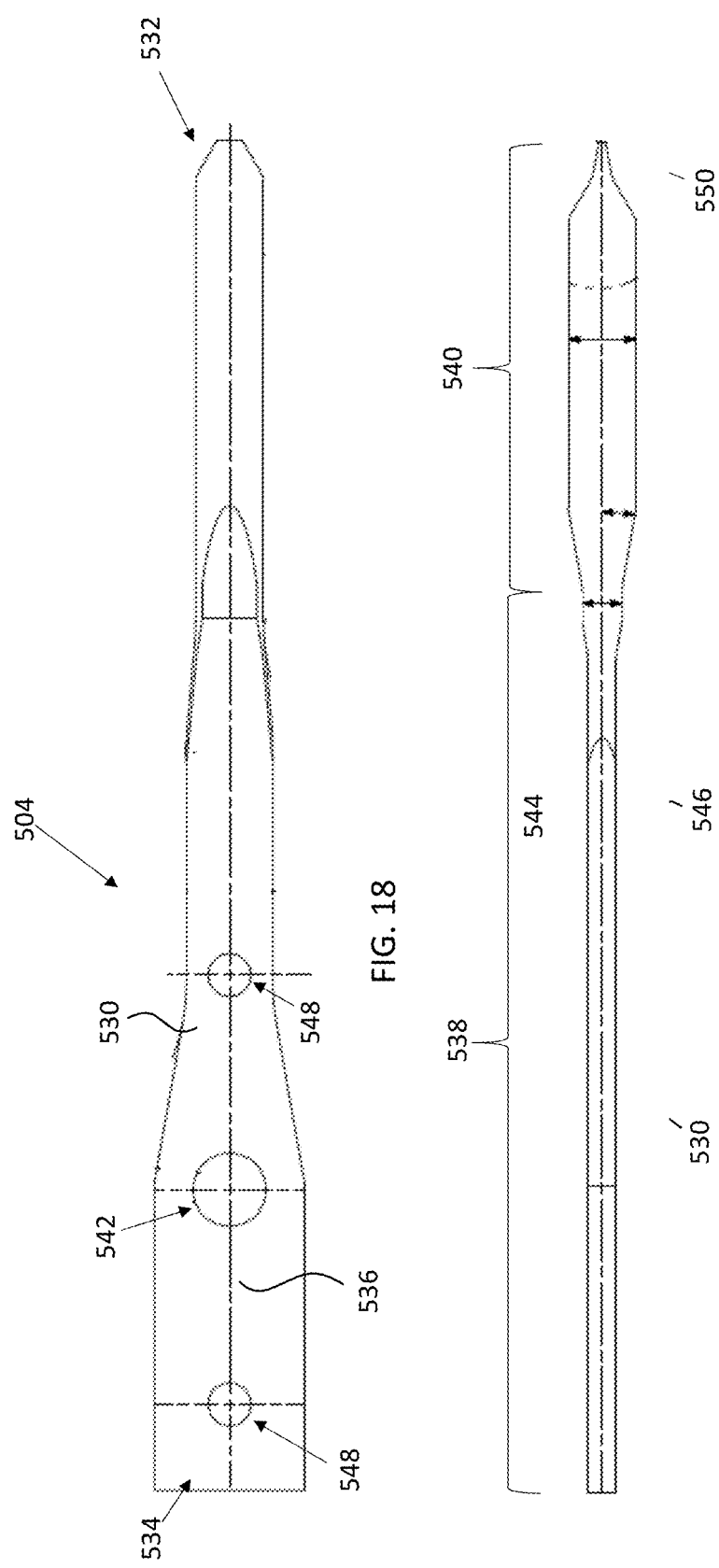

SYSTEMS, APPARATUSES, AND METHODS FOR CORRECTING A BONE DEFECT

FIELD

This disclosure relates generally to medical devices, and more specifically to implants for correcting bone deformity.

BACKGROUND

Tailor's bunion, or bunionette, is a condition of the human foot resulting in the inflammation of the fifth metatarsal bone at the base of the smallest toe. Tailor's bunions have proven to be difficult to repair due to the small size of the fifth metatarsal, especially at the distal metaphysis where many surgeons would prefer to make osteotomies. Further, the small cross-sectional area of the fifth metatarsal makes even the smallest screw difficult to place for a shifting head osteotomy (e.g., distal chevron, distal transverse cut), as the screws themselves take up a large portion of the remaining bone-on-bone contact.

SUMMARY

In some embodiments, an implant having a unitary body includes an intramedullary portion and an extramedullary portion. The intramedullary portion is sized and structured to be received within an intramedullary canal of a first bone and defines a longitudinal axis. The extramedullary portion includes a surface defining an axis that is disposed at an angle with respect to the longitudinal axis. An aperture defined along the extramedullary portion is sized and configured to receive a fastener therein for coupling the extramedullary portion of the implant to a second bone.

In some embodiments, the fastener is one of a locking fastener and a non-locking fastener.

In some embodiments, the extramedullary portion defining the aperture includes surface features permitting a fastener to be received at a plurality of angles relative to a central axis defined by the aperture.

In some embodiments, the surface features include a plurality of intermittent threads.

In some embodiments, the central axis defined by the aperture is positioned at an oblique angle with respect to the longitudinal axis defined by the intramedullary portion of the implant.

In some embodiments, the intramedullary portion has a circular cross-sectional geometry.

In some embodiments, a first end of the intramedullary portion of the implant tapers to a blunt end.

In some embodiments, a first end of the intramedullary portion of the implant tapers to a blade.

In some embodiments, the extramedullary portion of the implant is enlarged with respect to the intramedullary portion.

In some embodiments, the intramedullary portion of the implant includes one or more surface features disposed thereon for securing the implant within an intramedullary canal of a first bone.

In some embodiments, the surface features are selected from a group consisting of threads, splines, fins, and knurling.

In some embodiments, the first bone is a first bone fragment formed from a third bone, and the second bone is a second bone fragment formed from the third bone.

In some embodiments, the first bone and the second bone are two adjacent bones of a joint.

In some embodiments, a system includes an implant and a fastener. The implant has a unitary body including an intramedullary portion and an extramedullary portion. The intramedullary portion is sized and structured to be received within an intramedullary canal of a first bone and defines a longitudinal axis. The extramedullary portion is structured to be coupled to a second bone. An aperture defined by the extramedullary portion includes a surface defining an axis that is disposed at an angle with respect to the longitudinal axis. The fastener is sized and structured to be received within the aperture defined by the extramedullary portion of the implant.

In some embodiments, a central axis defined by the aperture is positioned at an oblique angle with respect to the longitudinal axis defined by the intramedullary portion of the implant.

In some embodiments, the surface of the extramedullary portion of the implant includes a planar surface.

In some embodiments, the fastener is one of a locking screw and a non-locking screw.

In some embodiments, the system includes an inserter having a body extending from a first end to a second end. At least one of the first end and the second end defines a pocket that is interconnected with a hole.

In some embodiments, the pocket is sized, dimensioned, and structured to receive at least a portion of the extramedullary portion therein such that, when the extramedullary portion of the implant is received within the pocket, the hole defined by the inserter aligns with the aperture defined by the implant.

In some embodiments, the system includes a guide having a body extending from a first end to a second end. A hole extends through the body from the first end to the second end, and at least one of the first end and the second end is at least partially threaded for engaging a thread defined by the aperture defined by the implant.

In some embodiments, a treatment method includes forming a longitudinal hole in a first bone; inserting an intramedullary portion of an implant into the longitudinal hole; forming a hole in a second bone based on a position of an aperture defined by an extramedullary portion of the implant relative to the second bone; and inserting a fastener through the aperture and into the second bone to couple the extramedullary portion of the implant to the second bone. The intramedullary portion of the implant defines a first longitudinal axis, and the extramedullary portion has a surface defining an axis that is disposed at an angle with respect to the longitudinal axis defined by the intramedullary portion.

In some embodiments, forming the hole in the second bone includes inserting a cutting tool into a guide hole defined by a guide, and further inserting the cutting tool into the guide hole until the cutting tool engages the second bone. The guide is coupled to the implant such that the guide hole is aligned with the aperture defined by the implant.

In some embodiments, the method includes disengaging the guide from the implant prior to inserting the fastener through the aperture.

In some embodiments, the method includes disengaging an insertion tool from the implant prior to inserting the fastener through the aperture.

In some embodiments, the longitudinal hole is formed using a broach.

In some embodiments, the first bone is a first bone segment formed from a third bone, the second bone is a second bone segment formed from the third bone, and the method includes performing an osteotomy on the third bone to form the first bone segment and the second bone segment.

In some embodiments, the third bone is a fifth metatarsal.

In some embodiments, the angle between the axis defined by the surface and the longitudinal axis is a right angle.

BRIEF DESCRIPTION OF THE DRAWINGS

FIG. 1 is a plan view of one example of an implant in accordance with some embodiments;

FIG. 2 is a side view of the implant illustrated in FIG. 1 in accordance with some embodiments;

FIG. 4 is a plan view of another example of an implant in accordance with some embodiments;

FIG. 5 is a side view of the implant illustrated in FIG. 4 in accordance with some embodiments;

FIG. 6 is a bottom-side plan view of one example of an inserter in accordance with some embodiments;

FIG. 7 is a side view of the inserter illustrated in FIG. 6 in accordance with some embodiments;

FIG. 8 is a top-side plan view of the inserter illustrated in FIG. 6 in accordance with some embodiments;

FIG. 9 is a detailed view of the engagement end of an inserter, taken along line 9-9 in FIG. 7, in accordance with some embodiments;

FIG. 10 is a cross-sectional view, taken along line 10-10 in FIG. 8, in accordance with some embodiments;

FIG. 11 is a side view of one example of a guide tool in accordance with some embodiments;

FIG. 12 is a front side plan view of the guide tool illustrated in FIG. 11 in accordance with some embodiments;

FIG. 13 is a sectional view of the guide tool illustrated in FIG. 11, taken along line 13-13 in FIG. 12, in accordance with some embodiments;

FIG. 14 is a top-side plan view of one example of a broach in accordance with some embodiments;

FIG. 15 is a side view of the broach illustrated in FIG. 14 in accordance with some embodiments;

FIG. 16 is a bottom-side plan view of the broach illustrated in FIG. 14 in accordance with some embodiments;

FIG. 17 is a side view of one example of a broach insert for a broach in accordance with some embodiments;

FIG. 18 is a top-side plan view of the broach insert shown in FIG. 17 in accordance with some embodiments;

DESCRIPTION

Figure 3:
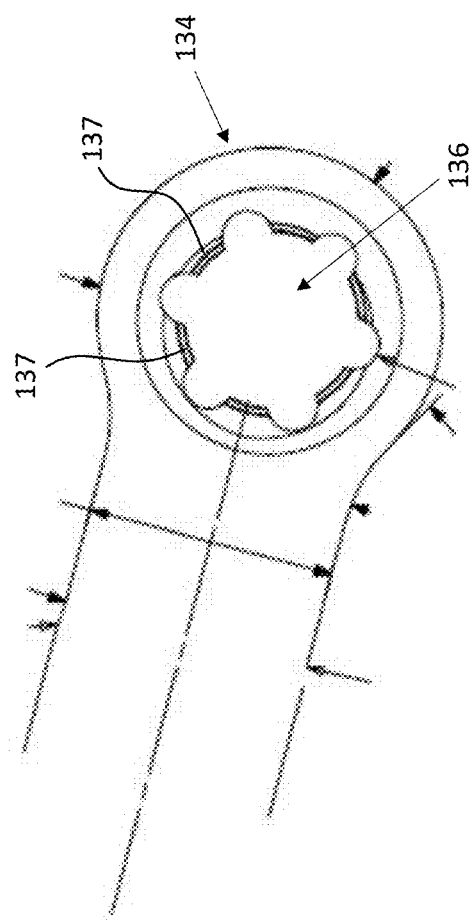
FIG. 3 is a detail view of the enlarged head of an extramedullary portion of the implant illustrated in FIG. 1 in accordance with some embodiments.

This description of the exemplary embodiments is to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. In the various drawings, like reference numerals indicate like items, unless expressly stated otherwise.

This disclosure provides implants, systems for installing the implants, and treatment methods for minimally invasive correction of Tailor's bunion (or of an analogous deformity in another joint). Although the drawings show application of the implant, inserter, and guide for treating a fifth metatarsal for the correction of Tailor's bunion, the implant, systems, and methods can be sized, configured, and tailored to treat other bones. For example, while the implants, systems, and methods may be described as being used to couple together first and second fragments or segments formed from a single bone, it should be understood that the implants, systems and methods may be used to extend across a joint thereby coupling together two adjacent and/or distinct bones (e.g., a metatarsal and a phalange). As such, the terms "first bone" and "second bone" may refer to two naturally distinct bones (e.g., a metatarsal and a phalange) and/or to two sections, portions, or fragments operatively formed from a single bone (e.g., a distal fragment and a proximal fragment formed from a metatarsal).

FIGS. 1-3 show a first example of the implant 100. FIG. 1 is a plan view of the implant 100, and FIG. 2 is a medial (or lateral) side view of the implant 100 of FIG. 1.

Figure 21:
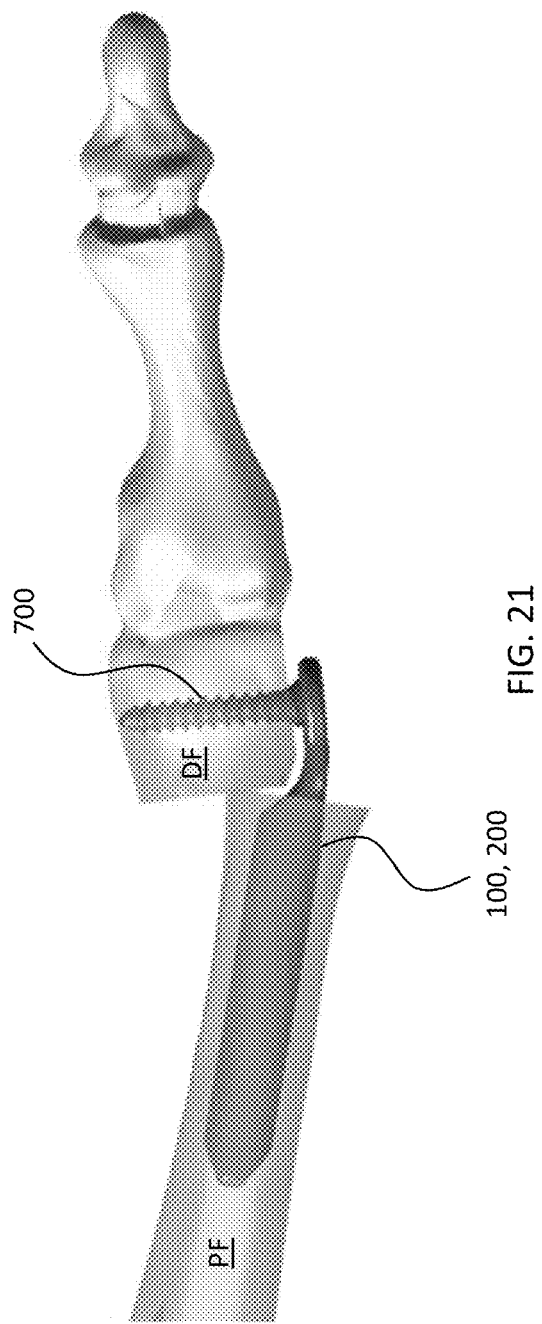
FIG. 21 illustrates one example of an implant joining two bone segments, sections, or fragments in accordance with some embodiments.

Referring to FIGS. 1-3, the implant 100 is illustrated having a unitary body including an intramedullary portion 110 connected to an extramedullary portion 130. The unitary body of implant 100 is configured to attach a first bone section, segment, or fragment to a second bone segment, section, or fragment. For example, implant 100 may be used to attach a proximal bone segment or fragment PF to a distal bone segment or fragment DF as best seen in FIG. 21. It should be understood that the implant 100 can be used on either left or right foot.

The intramedullary portion 110 defines a first longitudinal axis 120, which can be a central axis. The intramedullary portion 110 is configured for insertion into the first bone section (e.g., proximal fragment PF shown in FIG. 21). As best seen in FIGS. 1 and 2, intramedullary portion 110 may have a cylindrical geometric configuration with a one or more tapers or bevels 104 at first end (e.g., distal or insertion end) 102 to facilitate insertion of the intramedullary portion 110 into an intramedullary canal formed in a bone segment or fragment as will be discussed in greater detail herein. In some embodiments, the taper or bevel 104 terminates in a blunted tip 106. Although the cross-sectional geometry of intramedullary portion 110 is shown as being cylindrical, one of ordinary skill in the art will understand that the cross-sectional geometry of intramedullary portion 110 may be polygonal (e.g., triangular, rectangular, pentagonal, etc.) and/or include one or more protrusions or flat surfaces formed thereon to resist rotation of the implant 110 relative to the first bone segment or fragment. In some embodiments, the intramedullary portion 110 may be completely or partially threaded. In some embodiments, the intramedullary portion 110 may include one or more fins or protrusions extending outwardly therefrom to resist rotation of the implant 100 relative to the bone segment, section, or fragment.

The extramedullary portion 130 includes a bone contacting side or face 132 configured to abut a surface of a second bone section (e.g., a distal fragment DF as shown in FIG. 21). As best seen in FIG. 1, extramedullary portion 130 includes an enlarged head 134 defining a fastener aperture 136. In some embodiments, the enlarged head 134 has a circular geometry, although one of ordinary skill in the art will understand that enlarged head 134 may have other shapes. The at least one fastener aperture 136 defined by enlarged head 134 of extramedullary portion 130 defines an aperture axis 138 as best seen in FIG. 2. Fastener aperture 136 is sized and configured to receive a bone fastener (e.g., an "Ortholoc® 3Di™" locking screw sold by Wright Medical Technology, Inc. of Memphis, Tenn.), which may be used to secure the extramedullary portion 130 to the second bone section. For example, in some embodiments, the fastener aperture 136 includes a number of intermittent threads 137 that are formed by first tapping the aperture 136 and then transversely cutting through the threads to form the thread segments or intermittent threads 137 as best seen in FIGS. 1 and 3. In some embodiments, six transverse cuts are made to form the intermittent threads 137; however, one of ordinary skill in the art will understand that fewer or more transverse cuts can be made.

In some embodiments, the aperture axis 138 is oriented obliquely relative to the first longitudinal axis 120 as best seen in FIG. 2. In other embodiments (not shown), the aperture axis 138 is from about 90 degrees to about 180 degrees from the first longitudinal axis 120. For example, in some embodiments, the aperture axis 138 is oriented orthogonal to the first longitudinal axis 120.

The bone fastener may be disposed transversely or obliquely, relative to the fastener aperture 136. In some embodiments, polyaxial screws can be inserted at an angle of 0.0 to about 15 degrees with respect to the transverse axis of the fastener aperture 136. In some embodiments, polyaxial screws such as 3Di locking screws or non-locking screws sold by Wright Medical Technology, Inc. of Memphis, Tenn. may be utilized. As will be understood by a person of ordinary skill in the art, polyaxial screws may be inserted parallel to aperture axis 138 or at an angle (e.g., up to 15 degrees) relative to aperture axis 138.

As best seen in FIG. 2, a flat surface 140 is formed along a face of extramedullary portion 130 that is disposed opposite bone contacting side or face 132 and extends along at least a portion of the length of intramedullary portion 110. In some embodiments, flat surface 140 is disposed parallel to bone contacting side or face, which is disposed at an angle with respect longitudinal axis 120 defined by intramedullary portion 110. Put another way, in some embodiments, bone contacting side or face 132 and flat surface 140 are not arranged orthogonal or parallel to longitudinal axis 120, although one of ordinary skill in the art will understand that such arrangements in which bone contacting side or face 132 and flat surface 140 are positioned parallel to longitudinal axis are contemplated. In some embodiments, the bone contacting side or face is positioned at an angle of 15 degrees (or 165 degrees) relative to longitudinal axis 120 for correcting the valgus of the fifth metatarsal (metatarsus quintus valgus) at the level of the metatarsal head. In some embodiments, flat surface 140 includes first and second portions, which themselves may be disposed at angles relative to one another (i.e., the first and second portions are not co-planar).

FIGS. 4-5 illustrate another example of an implant 200 in accordance with some embodiments. FIG. 4 is a plan view of the implant 200, and FIG. 5 is a medial (or lateral) side view of the implant 200 of FIG. 4.

Like implant 100, implant 200 may have a unitary body including an intramedullary portion 210 that transitions into an extramedullary portion 230. Implant 200 is configured to attach a first bone section to a second bone section and can be used on either the left or the right foot.

The intramedullary portion 210 defines a first longitudinal axis 220, which can be a central axis, extending from first end (e.g., an insertion end) 206 and continuing to extramedullary portion 230. Intramedullary portion 210 may have a cylindrical geometric configuration with a one or more tapers or bevels 204 at first end 202 to facilitate insertion of the intramedullary portion 210 into bone segment as will be discussed in greater detail herein. In some embodiments taper or bevel terminates at a blade tip 206 that is more narrow and pointed than blunted tip 106. Although the cross-sectional geometry of intramedullary portion 210 is shown as being cylindrical, one of ordinary skill in the art will understand that the cross-sectional geometry of intramedullary portion 210 may be polygonal and/or include one or more protrusions, extensions, flat surfaces, or other anti-rotation features formed thereon to resist rotation of the implant 210 relative to a bone when implanted. Further, as discussed above with respect to implant 100, intramedullary portion 210 may be completely or partially threaded, or the intramedullary may including one or more fins or other protrusions extending from an external longitudinal surface thereof to engage the surrounding bone once implanted to resist rotation, improve fixation, and/or improve bone purchase.

Extramedullary portion 230 includes a bone contacting side or face 232 configured to abut a surface of the second bone section. As best seen in FIG. 4, extramedullary portion 230 includes an enlarged head 234 defining a fastener aperture 236 therethrough. Enlarged head 234 is shown with a circular geometry; however, one of ordinary skill in the art will understand that enlarged head 234 may have other geometrical shapes. The at least one fastener aperture 236 defines an aperture axis 238, as best seen in FIG. 5, which is oriented obliquely relative to the first longitudinal axis 220.

Fastener aperture 236 is sized and configured to receive a bone fastener, such as an "Ortholoc® 3Di™" locking screw sold by Wright Medical Technology, Inc. of Memphis, which may be used to secure the extramedullary portion 230 to a bone section. In some embodiments, the aperture axis 238 is aligned obliquely with the longitudinal axis 220 as shown in FIG. 2. In other embodiments (not shown), the aperture axis 238 is from about 90 degrees to about 180 degrees from the first longitudinal axis 220. For example, in some embodiments, the aperture axis 238 is oriented orthogonal to the first longitudinal axis 220. The bone fastener may be disposed transversely or obliquely, relative to the fastener aperture 236 and aperture axis 238. For example, in some embodiments, polyaxial screws can be inserted with an angle of 0.0 to about 15 degrees from the aperture axis 238.

As best seen in FIG. 5, a flat surface 240 is formed along a face of extramedullary portion 230 that is located on the opposite side of implant 200 as the contacting side or face 232. Flat or planar surface 240 extends across extramedullary portion 230 and at least a portion of intramedullary portion 210. In some embodiments, flat or planar surface 240 is disposed parallel to bone contacting side or face 232, which is positioned at an angle with respect longitudinal axis 220 such that contacting side or face 232 and flat surface 240 are not arranged orthogonal or parallel to longitudinal axis 220. In some embodiments, the contacting side or face 232 and flat surface 240 are positioned at an angle of 15 degrees (or 165 degrees) relative to longitudinal axis 220; however, a person of ordinary skill in the art will understand that contacting side or face 232 and flat or planar surface 240 may be disposed at other angles (e.g., 5 degrees, 10 degrees, 20 degrees, etc.) relative to longitudinal axis 220 defined by intramedullary portion.

Implants 100, 200 can comprise a metal, such as titanium, stainless steel, or CoCr. In some embodiments, the implants 100, 200 can comprise a metal substrate coated with or having an additional layer of hydroxyapatite (HA), titanium plasma spray (TPS)/vacuum plasma spray (VPS), roughened surface of resorbable blast media (RBM), a bioactive glass, an antimicrobial or antibiotic, or strontium. Alternatively, the implants 100, 200 can comprise a metal substrate with a composite coating or composite layer including HA on plasma, beads, an irregular sintered coating or TPS on an RBM-prepared substrate. In other embodiments, the metal substrate can have a porous coating. such as spherical bead, asymmetrical powder, or an irregular particle coating.

In some embodiments, the metal substrate of implants 100, 200 comprises a degradable (resorbable) material, such as a magnesium alloy, which may contain lithium, aluminum, rare earth metals (e.g., neodymium or cerium), manganese, zinc or other metals. In other embodiments, the resorbable material can include, but are not limited to polymer materials including a polylactide, polyglycolide, polycaprolactone, polyvalerolactone, polycarbonates, polyhydroxy butyrates, poly ortho esters, polyurethanes, polyanhydrides, and combinations and copolymers thereof, for example. In some embodiments, implants 100, 200 comprise a non-absorbable polymer, such as polyethereetherketone (PEEK), or an absorbable polymer composite, such as polylactic-acid (PLLA), a PLLA-beta-tricalcium-phosphate (β-TCP) blend, to list only a few possibilities.

In some embodiments, the implants 100, 200 comprise a biologic material. The biologic material can be a combination of Medical grade β-TCP granules and rhPDGF-BB solution, such as "AUGMENT®" bone graft material sold by Wright Medical Technology, Inc. of Memphis, Tenn. The biologic material can be applied, sprayed, or inserted at the wound site for bone in-growth, or can be provided as a coating on the implants or any or all portions of the implant system. In some embodiments, the biologic material is a coating containing osteoinductive or osteoconductive biological components. In some embodiments, the biologic material can include bone morphogenetic factors, i.e., growth factors whose activity are specific to bone tissue including, but not limited to, demineralized bone matrix (DBM), bone protein (BP), bone morphogenetic protein (BMP), and mixtures and combinations thereof. Additionally, formulations for promoting the attachment of endogenous bone may comprise bone marrow aspirate, bone marrow concentrate, and mixtures and combinations thereof.

The configuration of the implants 100, 200 advantageously provide an enhanced fixation of the distal fragment of the fifth metatarsal compared to the conventional buttressing k-wire technique. Further, the ability to use locking screws help prevent dorsal subluxation of the distal fragment as compared to the buttressing k-wire technique.

Inserter

In some embodiments, an inserter 300 may be provided for aiding a surgeon or other individual in implanting one of the implants 100, 200 in a patient. Such an inserter may be provided in a system or kit in accordance with some embodiments. One example of an inserter 300 is illustrated in the various views provided in FIGS. 6-10. Referring first to FIGS. 6-8, inserter 300 has a body 302 extending from a first end 304 to a second end 306 and defining a longitudinal axis 308. In some embodiments, end 304 is an impacting or handle end and end 306 is an engagement end as described below.

As best seen in FIGS. 6 and 7, impacting end includes a flange 310 that extends in a perpendicular direction with respect to the longitudinal axis 308 defined by inserter 300. Flange 310 includes an impacting surface 312, which is sized and structured to be impacted by a hand, mallet, hammer, or other impacting tool as will be understood by one of ordinary skill in the art. In some embodiments, flange 310 is supported or reinforced by one or more reinforcing ribs 314. Reinforcing rib(s) 314 may have triangular geometry as shown in FIG. 7, although other geometric configurations also are possible.

As best seen in FIGS. 6 and 8, one or more indents 316 may be provided along the length of the body 302. Indents 316 may be provided to enhance the ability of a surgeon or other user to grasp and manipulate inserter 300. In some embodiments, indents 316 have a rounded or curved configuration to provide for enhanced ergonomics.

Engagement end 306 is structured to engage an implant 100, 200 and defines a hole 318 (FIGS. 6, 8, and 9) and a pocket or channel 320 (FIGS. 6, 9, and 10). In some embodiments, hole 318 is dimensioned to provide clearance for receiving a mating end of a drill guide as discussed in greater detail herein. Pocket 320 is shaped and dimensioned to receive the enlarged head 134, 234 of extramedullary portion 130, 230 therein such that, when the enlarged head 124, 234 is received within pocket 320, the wall(s) 322 defining pocket 320 snugly engages the outer surface of enlarged head 134, 234 of implant 100, 200 to resist rotation of the implant 100, 200 relative to inserter 300.

As best seen in FIGS. 7 and 10, engagement end 306 may be angled relative to the longitudinal axis 308 of inserter 300. In some embodiments, the angle of engagement end 306 corresponds to the angle of the extramedullary portion 130, 230 of the implant 100, 200. Further, hole 318 defines an axis 324 that is arrange on body 302 of inserter 300 such that, when implant 100, 200 is engaged by engagement end 306 of inserter 300, the axis 324 is aligned with aperture axis 138, 238.

In some embodiments and as best seen in FIGS. 6, 8, 9, and 10, inserter 300 defines a hole or slot 330 along its length. The hole or slot 330 is sized and structured to receive a k-wire therein to temporarily fixate a distal fragment to another bone, e.g., the fourth metatarsal, as described in greater detail below. In some embodiments, an axis defined by hole or slot 330 is parallel to the axis 324 defined by hole 318. However, one of ordinary skill in the art will understand that hole or slot 330 may be oriented at other angles relative to the axis 324 defined by hole 318.

Inserter 300 may be provided in a wide variety of materials, including metal and/or plastic. In some embodiments, inserter 300 is formed from a material that may be sterilized such that the inserter may be provided in a sterilized package along with one or more implants and/or other devices described herein.

Guide Tool

FIGS. 11-13 illustrate one example of a guide tool 400 in accordance with some embodiments. Referring to FIG. 11, guide 400 includes a body 402 that extends from a coupling end 404 to a second end 406. In some embodiments, the body 402 of guide 400 includes one or more shoulders 410-1, 410-2 due to the body 402 including one or more segments having a reduced diameter relative to an adjacent segment. As shown in FIG. 11, the guide 400 is provided with three body segments 402-1, 402-2, and 402-3, with a shoulder 410-1 provided at the interface between body segments 402-1 and 402-2 and a shoulder 410-2 provided at the interface between body segments 402-2 and 402-3. One of ordinary skill in the art will understand that drill guide 400 may be provided with fewer segments and/or shoulders.

In some embodiments, distal segment 402-3 at coupling end 404 is at least partially threaded. For example and as illustrated in FIG. 11, threads 408 may extend partially or entirely along segment 402-3. Body segment 402-2, which is disposed between body segment 402-1 and body segment 402-3, may be provided with a smooth external surface. In some embodiments, body segment 402-3 has a cross-sectional diameter that is sized to be received within hole 318 of inserter 300 and has a thickness or width of segment 402-3 (e.g., the distance between shoulder 410-2 and end 404) dimensioned relative to the depth of hole 318 defined by inserter 300 (e.g., the distance D1 in FIG. 10) such that shoulder 410-2 is approximately planar with wall 328 of inserter 300 when the partially threaded portion of distal segment 402-3 is tightened onto the threaded aperture 136, 236.

Body segment 402-1, which in some embodiments has the greatest cross-sectional diameter, may include a surface texture formed on an external surface thereof to facilitate manipulate by a user. For example, the external surface 402-1 may include knurling, ridges, grooves, or any other suitable surface texturing as will be understood by one of ordinary skill in the art.

As best seen in FIGS. 12 and 13, drill guide 400 defines a central guide hole 412 that extends through the entirety of body 402. Guide hole 412 is sized and dimensioned to guide a suitable drill or other drilling or cutting tool for creating a pilot hole in a bone as discussed in greater detail below.

Broach

FIGS. 14-18 illustrate one example of a broach 500 including a handle 502 and a blade insert 504, in accordance with some embodiments. The handle 502 includes a body 506 extending from a first end 510 to a second end 512 substantially along a central longitudinal axis 514. The handle 502 defines at least one aperture 516 along its length extending from a first (e.g., upper) surface 518 to the second (e.g., lower or bottom) surface 520. In some embodiments, the handle 502 defines a slot or channel (not shown) inwardly extending from a first end 512 into the body 506 sized and configured to receive a portion of an insert 504 therein. In some embodiments, the channel is sized and configured to receive a portion of an insert 504 such that the aperture 516 is aligned with apertures formed in the insert 504 (as described in greater detail below) when the insert 504 is inserted into the channel. In some embodiments, the insert 504 is over-molded by handle 502.

End 510 of body 502 includes a flange 520 that extends perpendicularly with respect to the longitudinal axis 514 defined by body 502. Flange 520 includes an impacting surface 522. Impacting surface 522 is sized and structured to be impacted by a hand, mallet, hammer, or other impacting tool as will be understood by one of ordinary skill in the art.

In some embodiments, flange 522 is supported or reinforced by one or more reinforcing ribs 524. Reinforcing rib(s) 524 may have triangular geometry as illustrated in FIG. 15, although a person of ordinary skill in the art will understand that other geometric configurations also are possible.

As best seen in FIGS. 14 and 16, one or more indents 526 may be provided along the length of the body 502. Indents 526 may be provided to enhance the ability of a surgeon or other user to grasp and manipulate inserter broach 500. In some embodiments, indents 526 have a rounded or curved configuration to provide for enhanced ergonomics.

Turning now to FIGS. 17 and 18, one example of a blade or broach insert 504 is illustrated in accordance with some embodiments. Insert 504 includes a body 530 extending from a first end 532 to a second end 534 substantially along a central longitudinal axis 536. The insert 504 includes a first portion 538 configured to be coupled to a handle 502 and a second portion 540 configured to be at least partially inserted into a cut formed in a bone, such as a metatarsal, including the fifth metatarsal. Aperture 542 is positioned along the length of body 530 and enables over-molding material to flow within aperture 542. In some embodiments, one or more additional apertures 548 are defined by body 530 and are positioned along the body 530 of insert 504 such that, when the insert 504 is properly received within handle 502, apertures 548 are aligned with holes 516. The alignment of holes 516, 548 provides a passageway through broach 500 and enables a k-wire, pin, or other tool to be inserted through broach to provide some additional leverage for a user to dislodge broach from an intramedullary canal.

As shown in FIGS. 14-16, the insert 504 is configured to be coupled to the handle 502 to define a broach 500 configured to assist in the preparation of an intramedullary canal in a bone, such as a metatarsal, including a fifth metatarsal. As described in greater detail below, the second portion 540 of the insert 504 is configured to be inserted into a bone and leveraged to offset a first portion of a bone with a second portion of the bone to prepare an intramedullary canal. In some embodiments, a leading edge 550 of the insert 504 is configured to facilitate insertion into the bone. The leading edge 550 can be sharpened to define a cutting edge and/or include a thickness less than the thickness of the insert 504.

In some embodiments, the broach handle 502 (or a portion thereof) can be formed by injection molding material such as polycarbonate (PC), polyamide (e.g., Nylon), polyarylamide (e.g., PARA, Ixef, etc.), acrylonitrile butadiene styrene (ABS), and/or any other suitable injection molding material. The injection molding can be formed over one or more structural features, such as ribs, lattice, etc. or surface features, such as knurling, plasma spray, etc., to provide increased strength and/or to withstand forces applied during insertion of the broach 500 and formation of an intramedullary canal in a bone. In some embodiments, the insert 504 (or a portion thereof) is formed of a metal material formed by any suitable process, such as by stamping, bending, drilling, milling, turning, etc.

Assembly/System/Kit

Figure 19:
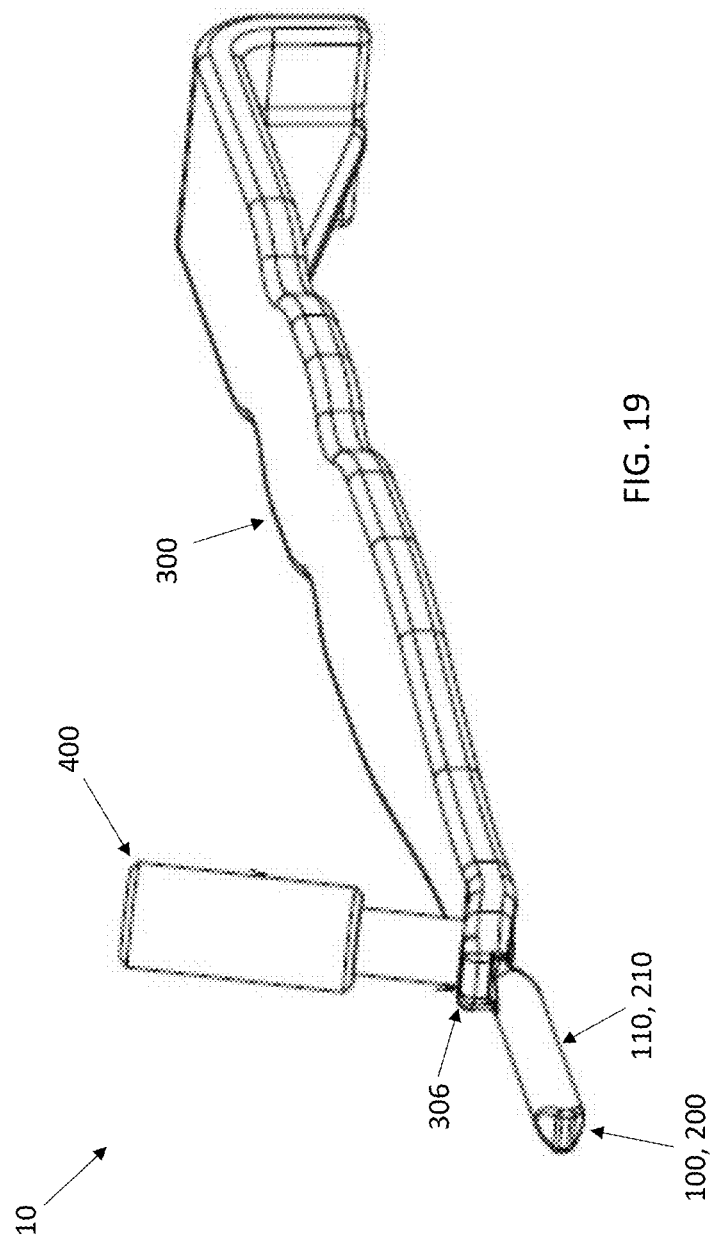
FIG. 19 is an isometric view of an assembly of an implant, an inserter, and a guide in accordance with some embodiments.

In some embodiments, the implant 100, 200, inserter 300, and guide 400 are provided in an assembled configuration, such as the configuration shown in FIG. 19. For example, the assembly 10 may be provided in sterilized package with each component having been sterilized after assemblage and packaging. As shown in FIG. 19, the extramedullary portion 130, 230 of implant 100, 200 is received within pocket 320 of inserter 300 such that intramedullary portion 110, 210 of implant is exposed by and extends away from end 306 of inserter 300.

More particularly, to provide the assembly 10, aperture hole 136, 236 of implant 100, 200 is aligned with hole 318 of inserter. Guide 400 is engaged with implant 100, 200 and inserter 300 by inserting body segment 402-3 into the aligned holes 136 (or 236) and 318 and then engaging the threads 408 of guide 400 with the thread segments 137 (or 237) of the implant. In some embodiments, threads 408 of guide 400 are engaged with thread segments 137 (or 237) by rotating guide body 402 relative to implant 100, 200 and inserter 300. The rotation of guide body 402 and thread engagement causes body 402 to advance into aperture 136 (or 236) and hole 318 of inserter 318 until shoulder 410-2 contacts the surface 328 of inserter 300. Once fully engaged, the relative positions of implant 100, 200, inserter 300, and guide are fixed in the assembled configuration 10 shown in FIG. 19.

In some embodiments, the various implants and/or tools are provided in a surgical kit in which each of the various components is individually placed within a sterilized package in a disassembled configuration and sterilized. For example, in some embodiments, one or more implants (of various sizes) may be provided in the kit with a correspondingly sized inserter, guide tool, and fastener(s). For example, the implant may be provided in 2 mm, 3 mm, 4 mm, 5 mm, and other cross-sectional diameters with inserters, guide tools, fasteners, and k-wire(s) configured for implanting these implants. Systems may also be provided in which one or more of the various components are separately packaged and then gathered at the time of surgery as will be understood by one of ordinary skill in the art. Various combinations of kits and/or individual components may be gathered together to provide a system. One of ordinary skill in the art will understand that there are numerous ways to provide a kit, system, and/or assembly and the foregoing examples are not limiting.

Method of Use/Treatment Method

Figure 20:
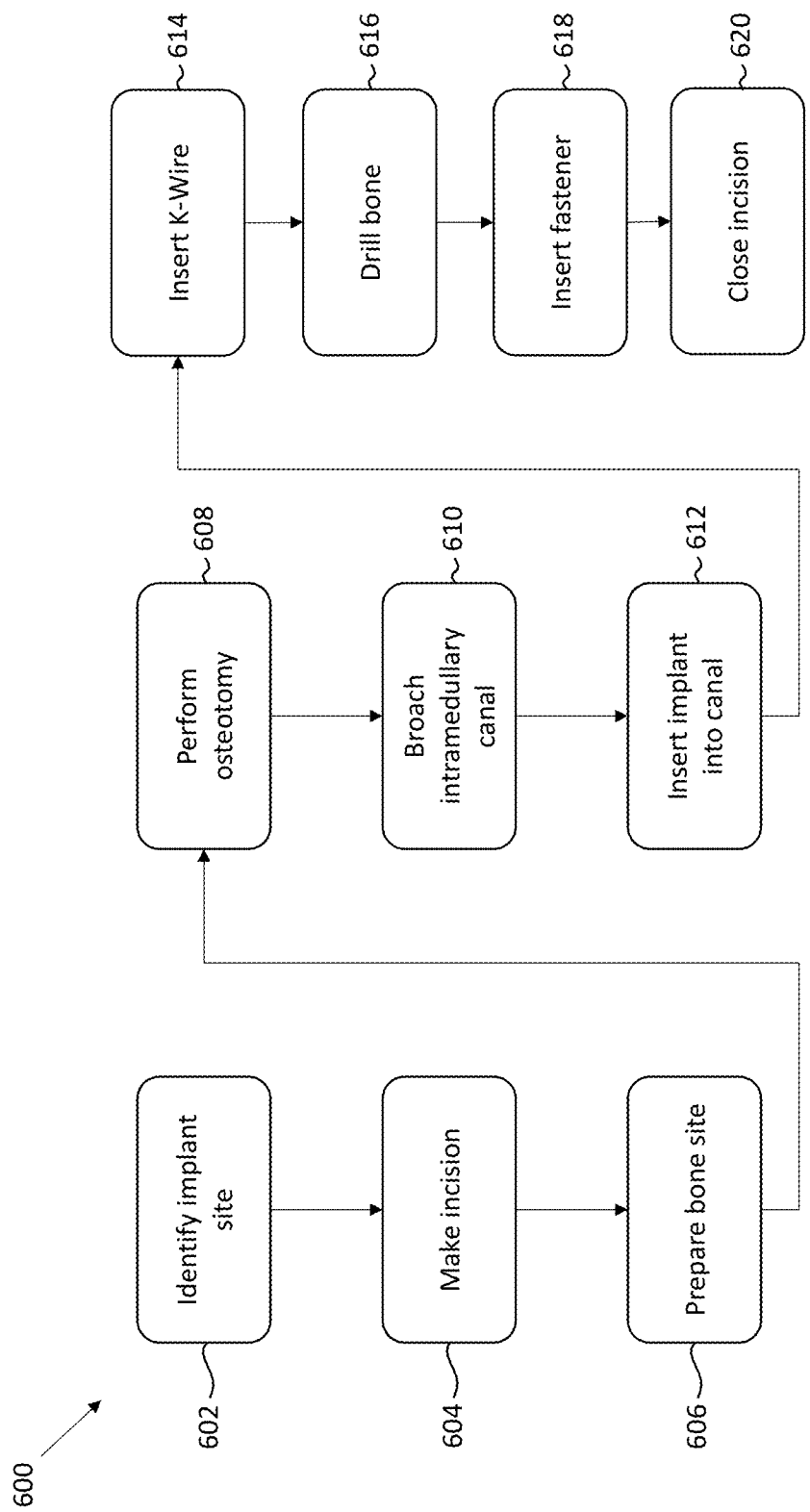
FIG. 20 is a flow diagram of one example of a method of treatment in accordance with some embodiments.

FIG. 20 is a flow chart of one example of a treatment method 600 in accordance with some embodiments, with FIGS. 20A-20G illustrating various steps performed of the method. At block 602, a patient is placed in a supine position on an operating table, and the metaphysis of the fifth metatarsal (or other targeted bone or implant site) is identified.

Figure 20B:
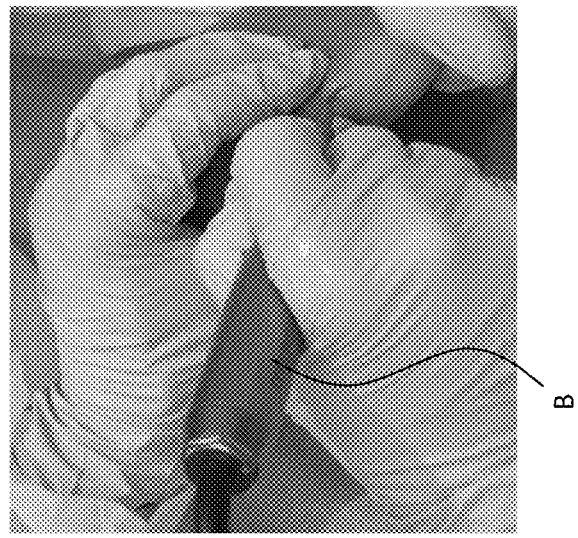
FIGS. 20A-20H illustrate various stages of the method of treatment in accordance with FIG. 20.
Figure 20A:
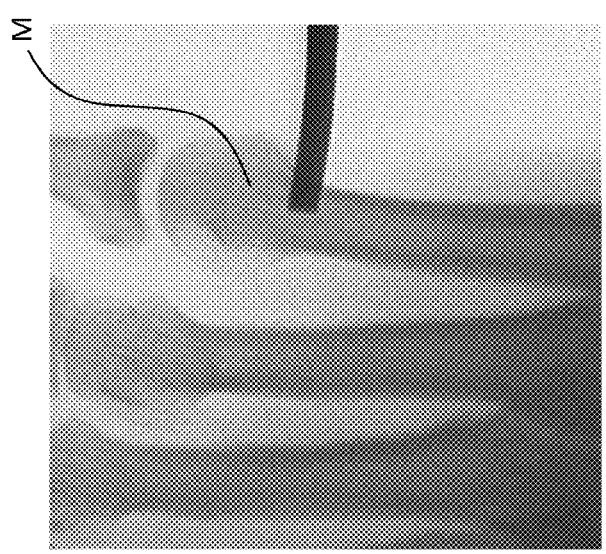

At block 604, a longitudinal incision is made proximal from the metaphysis of the fifth metatarsal head M, as shown in FIG. 20A, and extending distally. In some embodiments, the periosteum around the metaphysis is elevated using an elevator to allow for extracapsular osteotomy.

In situations where a large lateral prominence of the metatarsal head exists, the lateral eminence may be shaved down at block 606. The lateral eminence may be shaved down using a wedge burr or other suitable cutting or grinding tool as will be understood by one of ordinary skill in the art.

At block 608, an osteotomy is performed. In some embodiments, a transverse osteotomy is made using a Shannon burr B or saw at the level of the metaphysis. For example, the burr B may be plunged bi-cortically and then swept dorsally and plantarly to complete the cut. The plane of the cut may be perpendicular to the axis of the fifth metatarsal or to the axis of the fourth metatarsal at the osteotomy site. In some embodiments, a chevron osteotomy is performed instead of a transverse osteotomy. FIG. 20B illustrates an osteotomy being performed using a burr B in accordance with some embodiments.

Figure 20D:
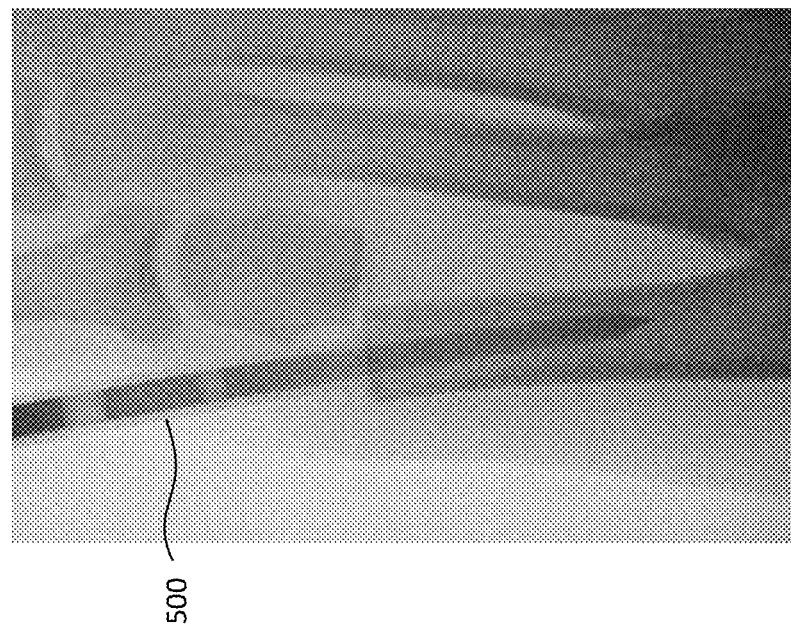
Figure 20C:
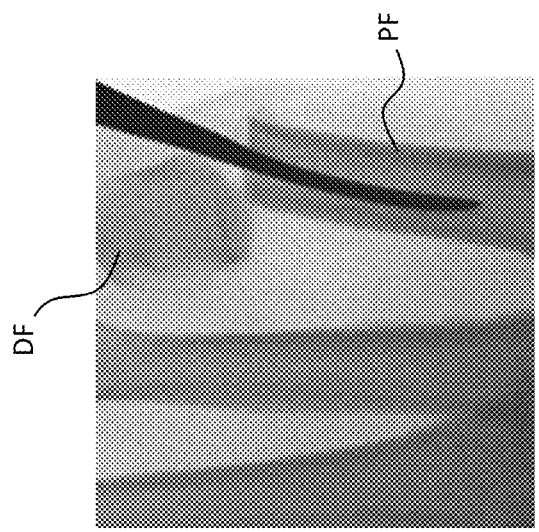
Figure 20F:
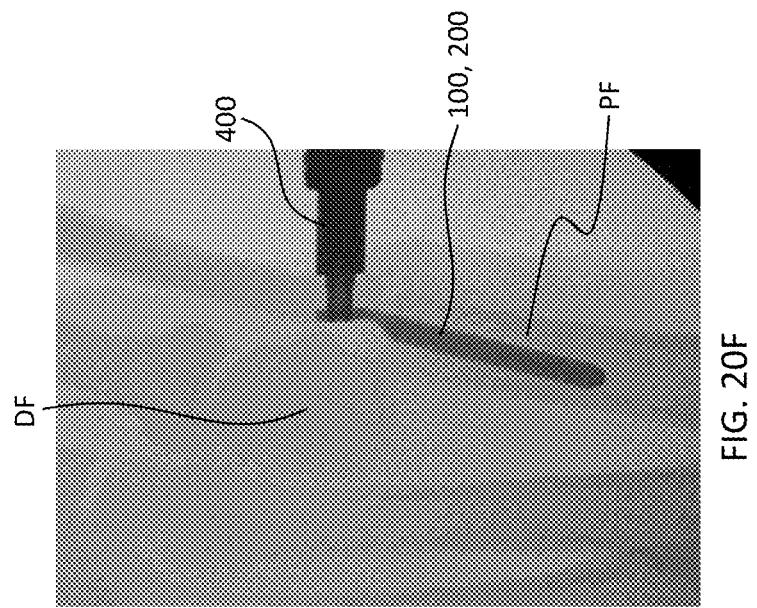
Figure 20E:
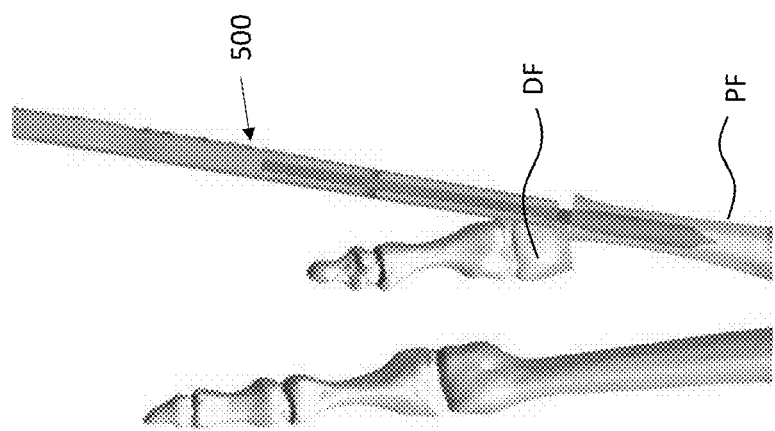

At block 610, the intramedullary canal of the proximal fragment PF is broached. In some embodiments, an initial broaching of the intramedullary canal may be performed using an elevator E after having moved the distal fragment DF out of the way as shown in FIG. 20C. FIGS. 20D and 20E illustrate the broach 500 being used to broach the intramedullary canal of proximal fragment PF. In some embodiments, a mallet, hammer, or other impaction device (not shown) may be used to achieve the desired broaching as will be understood by one of ordinary skill in the art. The impaction device may be used to hit impact surface 522 of broach 500 until the distal end of the broach handle 512 nearly touches the distal end of the proximal fragment PF. AP and ML radiographs may be checked to determine if the size of the broach adequately fills the intramedullary canal. If the broach does adequately fill the intramedullary canal, then the broach is removed. If the broach does not adequately fill the intramedullary canal, then a larger broach may be selected and the steps at block 610 may be repeated.

At block 612, the implant 100, 200 is inserted into the broached intramedullary canal. In some embodiments, the implant 100, 200 is pre-attached to inserter 300 and guide to provide the assembly 10 shown in FIG. 19 and as described above. The inserter 300 is used to guide implant 100, 200 into the broached intramedullary canal with the insertion end 106, 206 being introduced into the canal first as shown in FIG. 20F. A mallet (not shown) may be used to seat the implant 100, 200 fully (or properly) within the broached intramedullary canal. For example, the mallet may be used to tap on the impact surface 312 of inserter 300 until the inserter nearly touches the distal end of the proximal fragment.

Figure 20H:
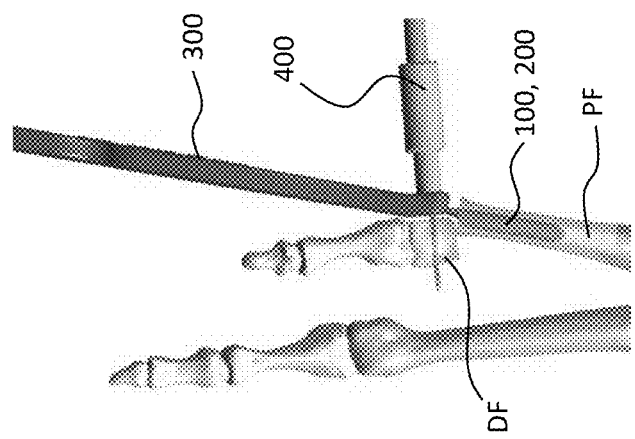
Figure 20G:
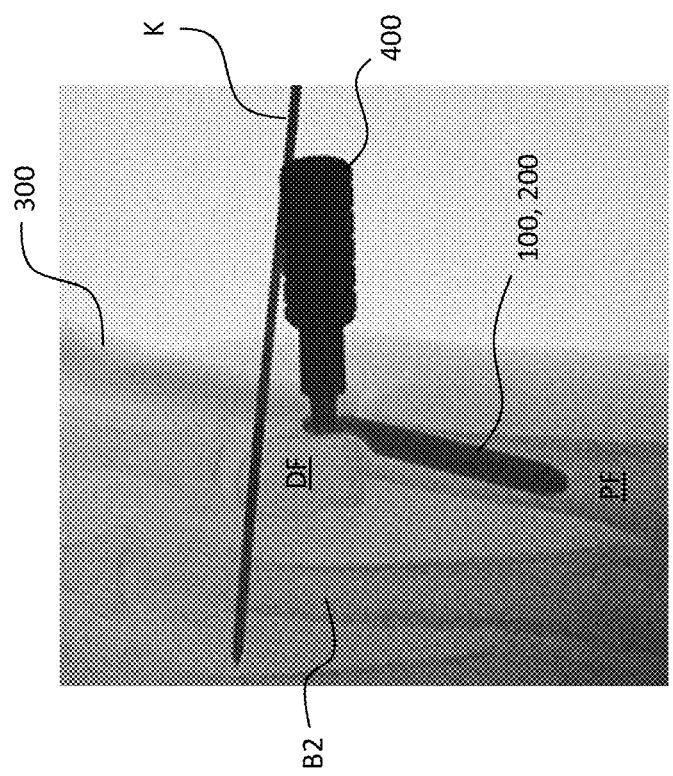

At optional block 614, a k-wire may be inserted through the hole or slot defined along the length of the inserter 300, through the distal fragment DF, and into a second bone, such as a fourth metatarsal. FIG. 20G illustrates the k-wire K being inserted through a hole or slot formed in inserter 300 and passing through the distal fragment DF and into second bone B2. In some embodiments, a surgeon may pinch medially of the distal fragment to ensure that the distal fragment is properly aligned in the dorsal-plantar direction and that the distal fragment laterally contacts the implant 100, 200. This pinching may be performed prior to k-wire insertion and/or as the k-wire is inserted.

At block 616, drilling for placement of the distal fragment screw is performed. For example, the distal fragment is drilled bi-cortically through the drill guide 400 as shown in FIG. 20H. In some embodiments, the drill guide 400 may be threaded directly into the thread segments 137, 237 within the fastener aperture 136, 236 having removed the inserter 300. However, in some embodiments, the drilling may be performed while the inserter 300 is still engaged with drill guide 400 and implant 100, 200 as shown in FIG. 20H. Once drilling is complete, the drill guide 400 may be removed from its engagement with the assembly 10 of the implant 100, 200 and inserter 300. Additionally, the inserter 300 may be removed from its engagement with the implant 100, 200.

At block 618, a fastener 700 is selected and used to secure the implant 100, 200 to the distal bone fragment DF. For example, a surgeon may use a locking or non-locking screw and inserts the selected fastener through fastener aperture 136, 236 and into the pre-drilled bone fragment. The k-wire K, if used, and inserter 300, if not yet removed, may then be removed.

At block 620, the incision is closed. In some embodiments, the distal-lateral corner of the proximal fragment is smoothed, using a burr, rasp, or other appropriate surgical tool, prior to closing the incision to avoid a sharp prominence after closure. One or more stitches also may be used to close the incision.

Although the subject matter has been described in terms of exemplary embodiments, it is not limited thereto. Rather, the appended claims should be construed broadly, to include other variants and embodiments, which may be made by those skilled in the art.

What is claimed is:

1. A system, comprising:
   an implant comprising:
      a unitary body including an intramedullary portion and an extramedullary portion, the intramedullary portion having a cylindrical geometry sized and structured to be received within an intramedullary canal of a metatarsal, the intramedullary portion defining a longitudinal axis and includes at least one flat such that the intramedullary portion tapers at a first end, the extramedullary portion structured to be coupled to a second bone and defining an aperture and including a surface defining an axis, and the axis defined by the surface of the extramedullary portion is disposed at an oblique angle with respect to the longitudinal axis of the intramedullary portion;
   an inserter comprising a body extending from a first end to a second end, wherein at least one end defines a pocket that is interconnected with a hole, wherein the pocket is sized and configured to receive at least a portion of the extramedullary portion therein, and wherein the first end of the inserter is positioned at an angle with respect to a longitudinal axis defined by the inserter such that, when the extramedullary portion of the implant is disposed within the pocket, the longitudinal axis of the intramedullary portion is parallel with the longitudinal axis defined by the inserter and the hole defined by the inserter aligns with the aperture defined by the implant; and
   a threaded fastener, the threaded fastener sized and structured to be received within the aperture defined by the extramedullary portion of the implant.

2. The system of claim 1, wherein a central axis defined by the aperture is positioned at an oblique angle with respect to the longitudinal axis defined by the intramedullary portion of the implant.

3. The implant system of claim 1, wherein the surface of the extramedullary portion of the implant includes a planar surface.

4. The system of claim 3, wherein the aperture defined by the extramedullary portion of the implant defines a central axis that is perpendicular to the planar surface.

5. The system of claim 4, wherein the aperture defined by the extramedullary portion of the implant includes a number of intermittent threads that are configured to engage the threaded fastener.

6. The implant system of claim 1, wherein the threaded fastener is one of a locking screw and a non-locking screw.

7. The implant system of claim 1, further comprising a guide, wherein the guide includes:
   a body extending from a first end to a second end, the body defining a hole extending through the body from the first end to the second end, wherein at least one of the first end and the second end is at least partially threaded for engaging a thread defined by the aperture defined by the implant.

8. The system of claim 1, wherein the second end of the body of the inserter includes a flange that extends at an angle with respect to the longitudinal axis of the inserter and includes an impacting surface.

9. The system of claim 1, wherein the extramedullary portion of the implant includes an enlarged, circular head that includes the aperture defined by the extramedullary portion of the implant.

10. A system, comprising:
    a unitary implant including:
       an intramedullary portion having a cylindrical shape that tapers to a blunt end, and
       an extramedullary portion extending away from the intramedullary portion at an angle, the extramedullary portion including an enlarged circular head having a planar surface, the enlarged circular head defining an aperture including a number of intermittent threads;
    a threaded fastener sized and structured to be received within the aperture defined by the enlarged circular head of the extramedullary portion of the unitary implant;
    an inserter including:
       a body extending from a first end to a second end, the first end of the body is positioned at an angle with respect to a longitudinal axis defined by the inserter and defines a pocket and a hole intersecting the pocket, the pocket sized and configured to receive the enlarged circular head of the extramedullary portion of the unitary implant such that, when the enlarged circular head of the extramedullary portion of the unitary implant is disposed within the pocket and the aperture defined by the enlarged circular head is aligned with the hole defined by the inserter, a longitudinal axis defined by the intramedullary portion of the unitary implant is disposed parallel to the longitudinal axis defined by the inserter; and
    a guide having a coupling end, the coupling end sized and configured to be received in the aperture defined by the circular head of the extramedullary portion of the unitary implant and in the hole defined by the first end of the body of the inserter to couple the inserter to the implant.

11. The system of claim 10, wherein the guide defines a guide hole that extends through the guide, the guide hole sized and dimensioned to guide a drill.

12. The system of claim 10, wherein the coupling end of the guide includes a thread configured to engage at least one of the intermittent threads of the aperture defined by the enlarged circular head.

13. The system of claim 10, wherein the threaded fastener includes at least one of a locking screw and a non-locking screw.

14. The system of claim 10, wherein the second end of the body of the inserter includes an impacting surface.

* * * * *